United States Patent [19]

Holmsen et al.

[11] 4,324,581

[45] * Apr. 13, 1982

[54] HERBICIDAL COMPOSITION FOR CONTROL OF SEDGES AND PERENNIAL GRASSY WEEDS

[75] Inventors: Theodore W. Holmsen, Clayton, Calif.; Keith C. Barrons, Holmes Beach, Fla.; Leonard L. Smith, Jr., Midland, Mich.

[73] Assignee: The Dow Chemical Company, Midland, Mich.

[ * ] Notice: The portion of the term of this patent subsequent to Apr. 25, 1995, has been disclaimed.

[21] Appl. No.: 900,035

[22] Filed: Apr. 25, 1978

Related U.S. Application Data

[63] Continuation-in-part of Ser. No. 751,631, Dec. 17, 1976, Pat. No. 4,086,081.

[51] Int. Cl.$^3$ .............................................. A01N 29/10
[52] U.S. Cl. ..................................................... 71/126
[58] Field of Search .......................................... 71/126

[56] References Cited

U.S. PATENT DOCUMENTS

| | | | |
|---|---|---|---|
| 3,373,011 | 3/1968 | Mussell | 71/126 |
| 3,930,835 | 1/1976 | Ozretich | 71/88 |
| 4,086,081 | 4/1978 | Barrons et al. | |

*Primary Examiner*—Catherine L. Mills

[57] ABSTRACT

Herbicidal composition used in method of preventing, for a time, growth of troublesome perennial grasses and sedges by incorporation of the composition into a surface layer of the soil of a field plot infested with the tubers and/or underground stems of such weeds and primarily above such tubers and stems. The composition is made up of α-(2,2,2-trichloroethyl)-m-chlorostyrene or α-(2,2,2-trichloroethyl)-m-bromostyrene or a co-mixture thereof and a suitable liquid or solid carrier to provide an emulsifiable concentrate, a wettable powder, a tank mix, a dust composition or a granulated solid composition.

12 Claims, No Drawings

HERBICIDAL COMPOSITION FOR CONTROL OF SEDGES AND PERENNIAL GRASSY WEEDS

CROSS REFERENCE TO RELATED APPLICATION

This application is a continuation-in-part of copending patent application, Ser. No. 751,631, filed Dec. 17, 1976, and now U.S. Pat. No. 4,086,081.

The application of Dalton L. Decker Ser. No. 751,630, filed even date herewith the parent hereof, describes and claims the novel compounds used according to the present invention in composition for the control of sedges and perennial grassy weeds.

BACKGROUND OF THE INVENTION

1. Field of the Invention

The invention relates to a composition containing certain derivatives of α-methylstyrene useful as highly effective herbicides in the control of perennial grasses and sedges in the presence of such valuable crops as cotton, peanuts, potatoes and sugar beets.

2. Description of the Prior Art

It has long been realized that those perennial grasses which spread by the growth of underground stems represent an especially difficult problem in the matter of herbicidal control. Included in these weedy grasses that are especially troublesome to eradicate are purple nutsedge, yellow nutsedge, bermudagrass, orchardgrass, knotgrass and cogongrass (alang-alang). In general, herbicides used heretofore to treat the above-ground portions of such weeds have, at best, killed the above-ground portions of the weeds without at all eradicating the underground portions. Furthermore, mechanical treatments such as discing of these grassy weeds seems merely to result in cutting the underground stems into small portions, each of which tend to grow readily, resulting in a multiplication of the weeds rather than eradication.

It is therefore desirable to provide a suitable herbicidal composition for controlling and if possible eradicating refractory weed species such as those identified hereinabove.

The compounds contained in the composition of present invention are embraced by the family of compounds a use of which is described in U.S. Pat. No. 3,373,011 issued Mar. 12, 1968. That patent describes the use of a number of substituted α-methylstyrene compounds in the control of grassy weeds. It is taught in the patent to use the substituted α-methylstyrenes for the control of small seeded grasses in preemergent applications as well as by discing into the soil around established crops. However, there is no teaching or suggestion in the said patent to employ the particular composition of the invention by incorporating it into soil containing perennial grassy weeds whereby the active ingredient is brought into a layer or band of soil primarily above the underground stems or tubers of weeds classed as perennial sedges and grasses resulting in the highly effective control thereof in a manner not achieved by the use of any of the other of the substituted α-methylstyrenes described in the said patent.

The compounds used in the composition of the present invention are also embraced by the family of compounds described in U.S. Pat. No. 3,391,203, issued July 2, 1968.

SUMMARY OF THE INVENTION

The present novel composition consists essentially of an α-(2,2,2-trichloroethyl)-metahalostyrene selected from the meta-chloro and meta-bromo compounds, both liquids, or a co-mixture thereof, in combination with any of (a) a surface active dispersing means with or without a small amount of water or organic liquid to provide an emulsifiable concentrate; (b) the foregoing plus a very finely divided solid agricultural carrier to provide a wettable powder; (c) either of the foregoing plus a substantial amount of water to form a tank mix for field application; (d) a finely divided solid agricultural carrier such as a clay to provide a dust composition; and (e) a finely divided solid agricultural carrier plus a binder such as starch in granulated and screened or ground form.

The concentration of the active ingredient to supply the desired dosage in a practical manner is generally from about 0.005 to about 90 percent by weight, but more generally is not over 50 percent by weight and in the case of dust compositions and granular compositions is in the range of about 0.1 to about 20 percent by weight. Concentrates such as emulsifiable concentrates and wettable powders preferably contain the active ingredient at a level in the range of from about 5 to about 98 percent by weight although a useful range of the binary combination of active ingredient and surface active dispersing means contains from about 0.1 to about 50 percent by weight of the dispersing means and the balance active ingredient. The finely divided solid agricultural carrier when employed generally constitutes from about 40 to about 99.5 percent by weight of the composition.

For field application an emulsion or dispersion of the active ingredient in water preferably contains from about 0.018 to about 0.145 percent by weight of the meta-halostyrene compound.

These compositions are highly useful in the control of those perennial grasses and sedges having substantial underground stem growth and/or tubers, upon incorporating the composition in the soil and primarily above such underground stems or tubers where the herbicide can intercept the shoots emerging from the underground stems and/or tubers. The composition containing active ingredient is incorporated into a shallow soil layer at a depth in the range of about ⅛ to about 6 inches at a herbicidal concentration in the soil, with respect to the perennial grassy weeds and/or sedges, in the range of about 0.25 to about 50 ppm of active ingredient, but at a rate of at least about 0.5 pound per acre and up to about 10 pounds per acre but usually less than about 4 pounds per acre of active ingredient.

DETAILED DESCRIPTION OF THE INVENTION

The compounds used in making up the composition of the invention are prepared according to the general methods described in U.S. Pat. Nos. 3,373,011, and, 3,391,203 the disclosures of which are incorporated herein by reference. The appropriate α-methyl-metahalostyrene is reacted with a halogenated compound such as $CCl_4$ in the presence of a free-radical initiator, which is preferably a catalyst system comprising an organic amine compound, such as piperidine, and a copper material such as cuprous chloride. It is postulated that a Diels-Alder addition of the halogenated compounds takes place across the double bond of the vinyl structure, followed by dehydrochloration resulting in the compound of the invention.

EXAMPLE 1

As an example of the preparation of the m-chloro ring substituted compound of the invention, 4.6 ml of piperidine (0.046 mole) was added in one portion to a mixture of ½ gram of cuprous chloride (0.0025 mole) in 216 grams of carbon tetrachloride (1.4 moles) containing 71 grams of mi-chloro-α-methylstyrene (0.46 mole). Upon warming the mixture to 75° C., an exotherm occurred and continued for 15 minutes during which time the green color of the solution turned brown. Refluxing was continued for 60 minutes and the brown reaction mixture was allowed to cool. Water was added, the layers separated, and the organic layer was washed once with water and dried over magnesium sulfate. Rotary evaporation gave 153 grams of a brown liquid. Flash, bulb-to-bulb, distillation gave 114 grams of a pale yellow liquid. A nuclear magnetic resonance (NMR) test indicated the sample contained 92 percent of 1-chloro-3-(1,3,3,3-tetrachloro-1-methylpropyl)benzene and 8 percent of the desired trichloroethylstyrene compound.

110 Grams of the pale yellow liquid was heated with 1.4 grams of cuprous chloride (0.007 mole) at 125° C. for 5 hours. After diluting the reaction mixture with methylene chloride, washing once with water and drying over magnesium sulfate, rotary evaporation gave 91 grams of a brown liquid. Short path distillation gave two fractions at 0.2 mm Hg pressure, a 78.8 gram fraction having a boiling range of 85°–88° C. and a 1.5 gram fraction having a boiling range of 88°–90° C. Gas chromatography indicated the first fraction contained a major proportion of the desired trichloroethylstyrene compound. A sample distilled through an 18 inch spinning band column had a boiling point of 92° C. at 0.35 mm Hg pressure. NMR indicated the sample was greater than 95 percent pure. Theoretical commposition of $C_{10}H_9Cl_5$ is carbon, 44.5 percent; hydrogen, 3.0 percent; and chlorine, 52.5 percent. Found: carbon, 44.4 percent; hydrogen, 3.0 percent; and chlorine, 52.4 percent.

EXAMPLE 2

Following the procedure of Organic Synthesis, Volume 40, page 7 (1960), 250 grams of $AlCl_3$ were stirred in a three-necked one liter flask equipped with a reflux condenser, a thermometer and a dropping funnel while 81 grams of acetophenone were added slowly over a 30 minute period. After stirring, an additional 15 minutes with the complexed mixture at about 50° C., 128 grams of liquid bromine was added from the dropping funnel over a period of about an hour, the outlet of the reflux condenser having been equipped with a scrubber for HBr and $Br_2$ fumes. The reaction mixture was warmed to about 60°–70° C. during the addition and was further heated to and maintained at 85° C. for one hour and then allowed to cool to ambient room temperature during a one and one-half hour period.

The reaction mixture was extracted twice with diethylether and the extracts combined and filtered. The combined extracts were washed with water, then aqueous $NaHCO_3$ solution according to the method of the said Organic Synthesis text and the separated organic liquid was dried for about 20 minutes over anhydrous $Na_2SO_4$. The ether component of the dried liquid was then evaporated off in a steam bath.

The foregoing process was repeated a second time and the resulting products found to contain about 90% 3-bromoacetophenone. The products were combined and distilled through a 30 inch Vigreux column, producing 180.1 grams of over 99% pure 3-bromoacetophenone.

23.8 Grams of magnesium turnings were covered with about 75 milliliters (ml) of diethyl ether and, while stirring the mixture, $CH_3Br$ gas was introduced through a delivery tube, the rate of addition of $CH_3Br$ being regulated to avoid excessive refluxing, the reaction flask being cooled with ice to facilitate more rapid addition of $CH_3Br$. After about one hour, the magnesium turnings could no longer be seen and the formation of Grignard reagent was believed to be complete. The delivery tube was replaced with a dropping funnel and the 180 grams of 3-bromoacetophenone were introduced dropwise while cooling the reaction flask. About 150 ml of tetrahydrofuran was also added as solvent and the addition of the 3-bromoacetophenone was completed in about 45 minutes.

Approximately 180 ml of saturated aqueous ammonium chloride solution was added dropwise, precipitating a solid phase. The organic liquid was decanted. The precipitate was washed twice with 150 ml portions of benzene and once with 100 ml of benzene. The decanted organic liquid and washings were combined and concentrated in a steam bath with the aid of a stream of nitrogen. When the volume of the liquid had been reduced to about 300 ml, the liquid was transferred to a 500 ml round bottom flask, about 10 grams of anhydrous $NaHSO_4$ was added and the liquid was distilled under a reduced pressure of 15–17 mm Hg through a 30 inch Vigreux column at a temperature ranging from 77° C. initially, to 99° C., yielding 129 grams of 3-bromo-α-methylstyrene in about 68% yield and having an index of refraction at 24° C. of 1.5775.

Fifty-nine grams of 3-bromo-α-methylstyrene were mixed with 196 ml of filtered $CCl_4$ and 0.6 gram of cuprous chloride in a 500 ml round bottom flask equipped with a reflux condenser, a thermometer and a dropping funnel. The contents of the flask were heated almost to reflux and 9.2 grams of piperidine were added, and, additional heating for about 45 minutes was carried out after the addition was completed and the initial refluxing subsided. The reaction was followed by G.L.C. (chromatography) until disappearance of starting material. After an additional 10 minutes of refluxing, the reaction was adjudged complete. The reaction mixture was allowed to cool and was washed with two 750 ml portions of 0.3 N aqueous HCl. The dilute acid washings were extracted with approximately 20 ml portions of $CCl_4$ which were combined with the washed organic layer and dried over anhydrous $Na_2SO_4$. The dried $CCl_4$ solution was subjected to flash distillation. After most of the solvent was removed, the pot temperature was increased to about 135° C. whereupon dehydrohalogenation took place. On subsequent fractional distillation of the material through a 30 inch Vigreux column at a reduced pressure of about 2.4 to 2.6 mm Hg and at a temperature in the range of 157°–160° C., 27.1 grams of product was obtained having a refractive index at 25° C. of 1.5892 and identified by infrared spectrometry as α-(2,2,2-trichloroethyl)-meta-bromostyrene.

For the sake of convenience, each of the compounds used in the composition of the invention will hereafter be referred to as "styrene" compound or "metahalostyrene compound" or "substituted α-methylstyrene" compound.

In particular it has been found that undesirable perennial sedges and grasses which are particularly noted for spreading by the growth of underground stems are controlled by the use of either of the said styrene compounds by preemergence methods wherein the compound contained in a composition of the invention is incorporated into the soil in a layer mostly or entirely above the underground stems of the weeds or directly contacted with said stems in a growth-suppressing or herbicidal amount. What constitutes a growth-suppressing or herbicidal amount of the styrene compound is dependent upon the plant species and the stage of growth thereof as well as the depth of incorporation of the styrene compound into the soil. Other factors, such as for example, the type of soil, whether a low organic matter soil (less than about 1% organic matter) or a high organic matter soil (greater than about 1% and typically up to about 6% organic matter) or the use of mechanical operations to substantially tear or cut up the underground stems of the perennial grasses and sedges and disturbance thereof or of the tubers, as in the case of the sedges, must also be considered.

In general, the perennial grasses are controlled by applying from about 1 to about 10 pounds or more per acre of the instant active compound by soil incorporation, although where it is desired to treat such perennial grasses in the presence of valuable crops a good measure of control while achieving selectivity is obtained at a dosage rate in the range of about 1 to 4 pounds per acre and preferably in the range of about 2 to 4 pounds per acre, and ordinarily applied before or during planting of the crop.

In employing the present composition in the control of sedges and perennial grasses, the composition in a form and dilution suitable for field application is applied to a field plot infested with the underground tubers and/or stems of sedges and/or perennial grasses. The composition is applied to the soil and incorporated therein mechanically, or, optionally, in some cases, by leaching, to provide the requisite thickness of treated surface band or layer containing the active compound in sufficient concentration above the underground tubers and/or underground stems to affect newly formed shoots arising from the tubers and/or stems. Either the newly formed shoots will be prevented from growing through the treated band or layer and emerging as above-ground growth or the emerged shoots will have severely limited growth.

A treated band from about ⅛ to about 6 inches deep will essentially lie mostly above the underground tubers and stems from which shoot growth is to be controlled. Generally, it is more economical and quite adequate to apply the substituted α-methyl styrene compound to a surface layer about ½ to about 3 inches thick. Within the treated layer, the concentration of active ingredient should be fairly uniformly spread, within the limits of ordinary agronomic practices, and at a herbicidal concentration in the range of about 0.25 to about 50 ppm and more preferably about 1 to about 25 ppm, the most preferred adequate dosage being somewhat towards the middle to lower end of such range, e.g., about 1 to about 10 ppm, soils of low organic matter content, i.e., less than about 1% by weight organic matter, while for soils of higher organic matter content a preferred adequate dosage will be selected from the upper part of said range, e.g. about 2 to about 25 ppm. Generally it is necessary to employ sufficient of the present composition to provide at least 0.5 pound of styrene compound per acre and up to about 4 pounds per acre in the presence of valuable tolerant crops, though up to 10 pounds per acre or more may be used if there is no concern for such crops.

The mode of operation of the active ingredient of the present composition in controlling sedges and perennial grasses is not completely understood but is believed to arise from ready uptake of the active ingredient by growing underground shoots of such weeds and resulting herbicidal growth altering action upon such shoots. This action either prevents growth of the shoots to above-ground levels for periods of several weeks to 12 weeks or more or severley restricts the growth of the emerged shoots for a like period. The active ingredient does not appear to be taken up effectively by either roots or above-ground plant parts of sedges or perennial grasses.

In any event, it is generally adequate to apply from about 0.5 to about 4 lbs per acre of styrene compound in from about 10 to about 27,000 gallons of liquid carrier or 10 to about 2,000 pounds of finely divided solid carrier, usually by pre-planting incorporation, to a depth of about 3 inches, by mechanical discing or rototilling unless the soil is light and of low organic matter content when it is usually adequate to broadcast or very lightly incorporate the styrene compound in the field plot and to leach in the styrene compound by sprinking the field plot with about an inch or two of water. More typically the styrene compound is supplied at the indicated dosage range in about 20 to 350 gallons of liquid carrier.

As indicated hereinabove, the present composition may be a liquid or dust composition containing the styrene compound. In such, compositions, the styrene compound can be modified with one or a plurality of herbicide carriers such as water, petroleum distillates or other liquid carriers; and cooperating substances such as surface active dispersing agents, and finely divided solids. Depending upon the concentration of the styrene compound, such augmented compositions are adapted to be distributed in the soil without further modification, or employed as concentrates subsequently diluted with additional herbicide carrier to produce the ultimate treating compositions.

The present compositions then comprise the styrene compound and surface active dispersing agent, with or without other herbicide carrier, or, in the case of solid carriers, with or without surface active dispersing means. Such compositions facilitate the use of the styrene compound and there is obtained a result which is much improved over the result when the unmodified styrene compound is employed for herbicidal purposes in controlling sedges and the perennial grasses referred to above. More particularly, the utilization of an herbicide carrier permits the growth-altering amount of styrene compound to be mixed in such quantity of all of the treating material with adequate coverage of all underground plant parts or adequate mixture in the growth medium can be obtained at the appropriate depth and thereby the desired growth-altering benefits of the styrene compound can be completely utilized. Some of these improved results of the utilization of herbicide carrier are obtained when employing the carrier in relatively small, but effective amounts. Generally however, the improvement is best obtained by employing, for example, surface active dispersing agents in an amount sufficient to emulsify the styrene compound with water, for example, an amount which represents from 0.1 to 50 percent, by weight, of the total treating material or a finely divided carrier solid in an amount which represents from 40 to 99.5 percent, by weight, of the total treating material.

The exact concentration of the styrene compound to be employed in a composition for application to plants or growth media is not critical and can vary considerably provided the required dosage of effective agent is supplied on the plant part treated or within the growth media. The concentration of starting compound in liquid compositions employed to supply the desired dosage generally is from about 0.005 to 50 percent by weight, although concentrations as high as 90 percent by weight are sometimes conveniently employed. In finely divided solid carrier compositions, the concentration of styrene compounds can be from 0.1 to 20 percent by weight. In compositions to be employed as emulsion concentrates, the styrene compounds can be present in a concentration of from about 5 to about 98 percent by weight.

The quantity of treating compositions to be applied can vary considerably provided that the required dosage of active ingredient is applied in sufficient of the finished composition to cover adequately the area to be treated or to facilitate the penetration and distribution of the active agent in growth media. The required amount of the active agent can conveniently be supplied per acre treated in from about 10 to about 27,000 gallons or more of the liquid carrier or in from about 10 to about 2,000 pounds of the finely divided solid carrier.

Liquid compositions containing the desired amount of active ingredient can be prepared by dissolving the styrene compound in an organic liquid carrier in admixture with a surface active dispersing means whereby the composition is dispersible in water as an emulsion, or, by dispersing the styrene compound directly in water with the aid of a suitable surface active dispersing agent such as an ionic or non-ionic emulsifying agent.

Suitable organic liquid carriers include the agricultural spray oils and the petroleum distillates such as diesel fuel, kerosene, fuel oil, naphtha, acetone, chlorinated solvents, xylene, ether of ethylene glycol and Stoddard solvent. Among the organic liquid carriers, the petroleum distillates are generally preferred.

The aqueous compositions can contain one or more water-immiscible solvents for the styrene compound. In such compositions, the carrier comprises an aqueous emulsion, i.e., a mixture of water, emulsifying agent and water-immiscible solvent. The choice of dispersing and emulsifying agent and the amount thereof employed is dictated by the nature of the composition and by the ability of the agent to facilitate the dispersion of styrene compound in the carrier to produce the desired composition.

Dispersing and emulsifying agents, i.e., surface active dispersing means, which can be employed in the compositions particularly in the preparation of emulsifiable concentrates include the condensation products of alkylene oxides with phenols and organic acids such as nonylphenol ethoxylates, alkyl aryl sulfonates such as the isopropyl amine salt or the calcium salt of dodecylbenzene sulfonic acid, polyoxyalkylene derivatives of sorbitan esters, castor oil ethoxylates, complex ether alcohols, mahogany soaps, block copolymers of polyethylene oxide and polypropylene oxide and the like, and combinations or blends thereof.

The nonionic dispersing agents which contain ethylene oxide units in the molecule can generally be designed to include the requisite amount of ethylene oxide or propylene oxide units to obtain the desired hydrophylic-lipophilic balance in the dispersing agent molecule, greater proportions of ethylene oxide providing increased hydrophilic nature. The desired hydrophylic-lipophilic balance may also be obtained upon blending appropriate nonionic dispersing agents with or without an anionic dispersing agent in addition.

A specific example of a suitable emulsifiable concentrate composition of the invention contains a blended, suitably balanced admixture of calcium salt of dodecylbenzene sulfonic acid, a block copolymer of ethylene oxide and propylene oxide sold by Thompson-Hayward Chemical Company as T-Mulz 704H and a sorbitol ester ethoxylate sold by ICI United States, Incorporated as Atlox 938. The composition of the concentrate is set forth as follows by weight:

| %   | Component                               |
|-----|-----------------------------------------|
| 3.3 | Ca salt of dodecylbenzene sulfonic acid |
| 1.8 | T-Mulz 704H block copolymer             |
| 0.9 | Atlox 938 sorbitol ester ethoxylate     |
| 64  | Styrene compound                        |
| 30  | Organic solvent                         |

The organic solvent in such concentrate is selected from mineral spirits, xylene, kerosene, an ethylene glycol or propylene glycol ether of a lower alkanol having about one to six carbon atoms, or a chlorinated hydrocarbon solvent such as ethylene dichloride or 1,1,1-trichloroethane.

In the preparation of water dispersible solid or granulated compositions, the active ingredient is dispersed in and on a finely divided solid agricultural carrier such as clay, talc, chalk, gypsum, bentonite, fuller's earth, attapulgite and the like. In such operations the finely divided carrier is mechanically mixed or ground with the styrene compound and combined during grinding or subsequently with surface active dispersing means with or without a small amount of water or non-aqueous liquid selected from the organic liquid carriers listed above. The amount of surface active dispersing means is sufficient to provide emulsification or dispersion of the meta-halostyrene compound and the solids, generally from about 1 to about 10 percent of the water dispersible concentrate, as a concentrate as well as subsequently as a tank mix. The objective is to obtain the desired amount of active ingredient in a composition adapted to be employed for the suppression of the growth of the said sedges and perennial grassy weeds.

Wherein the present composition is used for its particularly valuable property as a herbicide effective against perennial sedges and grasses, it is highly useful to prepare a dust composition that is described and to granulate the same into granular form by well known granulation methods. Such a dust composition whether or not granulated is satisfactorily used for soil incorporation per se and may also be combined with other agricultural materials intended to be applied to the soil such as fertilizers, soil conditioning agents and the like. Similarly, the liquid compositions described may be combined with other agricultural materials such as fertilizers, fungicides, insecticides, other herbicides, soil conditioning agents, and the like.

EXAMPLE 3

As an example of the use of the styrene compound in a composition according to the invention in the control of a perennial sedge a liquid formulation was prepared containing two pounds per gallon of α-(2,2,2-trichloroethyl)-meta-chlorostyrene dispersed in water with the aid of a wetting agent, i.e., a surface active dispersing means known as Tween 20, a polyoxyalkylene derivative of sorbitan ester. The liquid composition was incorporated in a field plot with a tractor-powered rototiller which deposited the composition at a depth of 2 to 3 inches into the soil in 20 inch bands and above most of the nutsedge tubers. The spray volume was 20 gallons per acre resulting in a dosage rate of 4 pounds of active ingredient per acre. The soil bed was culti-packed immediately after incorporation of the herbicide and immediately before planting. Cotton was planted in the so-treated soil, a commercial fungicide being applied at the time of planting. Cotton seeds were planted 1.5 inches deep. Control of yellow nutsedge was evaluated 4 weeks after treatment and found to be 100 percent effective. Evatreatment and found to be 100 percent effective. Evaluations 6 weeks and 10 weeks after planting likewise showed 100 percent control. Twenty weeks after planting 94 percent control of the yellow nutsedge was still evident while substantially no adverse effects on the cotton seedlings or plants was observed.

Substantially the same fine results are observed upon treating field plots containing bermudagrass, orchardgrass, knotgrass, cogongrass, or purple nutsedge, upon using the discing in method of soil incorporation to incorporate compositions of the invention containing, respectively, α-(2,2,2-trichloroethyl)-meta-chlorostyrene, and α-(2,2,2-trichloroethyl)-meta-bromostyrene, or a co-mixture thereof, in respective field plots.

EXAMPLE 4

Control of *Paspalum Dilitatum* (Orchard Grass)

Orchard grass rhizome clumps were dug on the south side of California Highway 128, 1 mile east of U.S. 5 between Davis and Winters. The tops were cut from the clumps. The rhizome clumps were put in flats of moist sand and maintained for 6 days before testing. Two clumps were placed on a sandy loam soil (0.8% organic matter) in a 10-cm diameter pot and then covered with soil to within 2.5 cm of the top of the pot. The soil surface was sprayed with a solution of α-(2,2,2-Trichloroethyl)-m-chlorostyrene in 50 percent acetone: 50 percent water containing 0.2 percent Tween 20 and then the sprayed surface covered with about 1 cm of untreated soil. The pots were watered and maintained under prevailing greenhouse conditions. There were 5 pots of plants treated with each rate of styrene compound and 5 pots treated with a formulations blank.

Five weeks after treatment, the plants were examined and then cut off at the soil surface and weighed.

| Styrene Compound Lbs/Acre | Top Growth, Fresh Weight Grams/5 Pots |
| --- | --- |
| 4 | 20.64 |
| 2 | 76.54 |
| 1 | 72.73 |
| 0.5 | 100.57 |
| 0.25 | 81.90 |
| 0 | 89.46 |

Calculated $GR_{50}$ = 2.76 lbs/Acre
$GR_{80}$ = 5.75 lbs/Acre

EXAMPLE 5

Control of Perennial Grasses and Sedges

The method of Example 4 was substantially followed in tests against orchard grass while in additional tests the application of styrene compound was made also in a similar manner to replicated pots containing, respectively, yellow nutsedge, and short lengths or segments of rhizomes of knotgrass, and, bermudagrass, having 3 to 5 nodes per pot, two pots per treatment and 5 untreated pots in each case as controls. The styrene compound used in these tests was α-(2,2,2-trichloroethyl)-m-bromostyrene. On evaluation three weeks after treatment, the following results were observed.

| Rate of Styrene Compound Lb/Acre | Percent Control | | | |
| --- | --- | --- | --- | --- |
| | Orchard-grass | Yellow Nutsedge | Knot-grass | Bermuda grass |
| 4 | 80 | 100 | 100 | 90 |
| 2 | 0 | 100 | 70 | 70 |
| 1 | 0 | 30 | 50 | 20 |
| 0.5 | 0 | 0 | 30 | 0 |

EXAMPLE 6

Control of Knotgrass (*Paspalum Distichum* L.)

Rhizomes were dug in the field and 2 to 3 node segments planted in pots and covered with approximately ¼ inch of soil. This surface was sprayed with an acetone emulsion of α-(2,2,2-trichloroethyl)-m-chlorostyrene in 50% acetone, 0.1% Tween 20; remainder water. 2.5 ml of solution was applied to a 4-inch round pot containing a loam soil (0.8% organic matter). The sprayed surface was then covered with ½ inch of soil. The pots were placed in the greenhouse to grow. Six weeks after treatment, the pots were evaluated for growth. There were 10 pots for each treatment.

| Styrene Compound Lbs/Acre | Top Growth, Fresh Weight Grams/10 pots |
| --- | --- |
| 4 | 0.04 |
| 2 | 2.87 |
| 1 | 20.33 |
| 0.5 | 33.56 |
| 0.25 | 52.42 |
| 0 (Control) | 66.63 |

$GR_{80}$ is 1.06 lb/Acre

EXAMPLE 7

Control of *Cynodon Dactylon* (L.) Pers. (Bermuda Grass)

Bermuda grass rhizomes were dug, and healthy ones were cut into segments containing 3-4 nodes. The rhizome segments were placed on a loam soil (0.8% organic matter) in a 10-cm diameter pot and then covered with about 2 cm of soil. The soil surface was sprayed with a solution of α-(2,2,2-trichloroethyl)-m-chlorostyrene in (50 percent active:50 percent water containing Tween 20). The sprayed surface was cultivated with a spatula to a depth of about one half inch. The pots were watered and placed in a greenhouse under prevailing conditions for growth. Four and one-half weeks after treatment, the plants were examined and then cut off at the soil surface and weighed. There were 10 pots per treatment.

| Styrene Compound Lbs/Acre | Number of Emerged Shoots | Fresh Weight of Shoots - gm |
|---|---|---|
| 4 | 4 | 6.47 |
| 2 | 8 | 24.61 |
| 1 | 13 | 35.25 |
| 0.5 | 27 | 63.72 |
| 0.25 | 40 | 66.76 |
| 0 | 46 | 80.24 |

Calculated $GR_{80}$ = 2.46 lbs/Acre
$GR_{50}$ = 0.93 lb/Acre

EXAMPLE 8

Control of *Imperata Cylindrica* (L.) Beauv. (Cogon Grass or Alang Alang)

Rhizomes were dug in Mobile, Alabama and air-mailed to Walnut Creek, Calif. Two healthy rhizome segments containing 3 to 4 nodes each were planted and treated with α-(2,2,2-trichloroethyl)-m-trichlorostyrene in a manner similar to that described in Example 4. Seven weeks after treatment, the 10 pots treated with 4 lbs/Acre of styrene compound had no cogon grass growing. Plants growing in untreated pots are vigorous with many 8 to 10-cm branches per plant.

EXAMPLE 9

A field plot of sandy loam soil of low organic matter and infested with purple nutsedge was prepared for the planting of cotton and 2 pounds per acre of α-(2,2,2-trichloroethyl)-m-chlorostyrene was broadcast and disced in with a disc set to penetrate 6 inches. Incorporation of most of the styrene compound was in the surface layer 3 inches deep, though some reached a depth of about 6 inches. The cotton seeds were then planted. In the space of a little over two months spaced apart rains of 0.44 inch, 0.76 inch and 0.55 inch occurred. About one week after the last rain, the results of the treatment were evaluated. Rating herbicidal control on a scale of 0 to 10 with 10 complete control, purple nutsedge control was rated 9.8, while slight phytotoxicity was observed in the cotton plants with a rating of 1.3. An untreated plot showed a rating on purple nutsedge of 2 and on cotton 0.3.

EXAMPLE 10

The procedure of Example 9 was substantially repeated except that the plot was infested with yellow nutsedge and barnyardgrass and incorporation was by Lilliston harrow to a depth of 1 to 2 inches was carried out in respective plots with 1, 2 and 4 lbs per acre of styrene compound. Rains occurred of 0.76 inch and 0.3 inch magnitude. A little over two months after treatment and about one week after the second rain, the results were evaluated. With 1 lb/acre active yellow nutsedge control was rated 9.0 and barnyardgrass 7.5 while the phytotoxic effects on the cotton was rated 1.5. With 2 lbs/acre active yellow nutsedge, control was rated 9.3, barnyardgrass 9.8 and no phytotoxic effects on cotton were noted. With 4 lbs/acre active yellow nutsedge control was rated 9.5, barnyardgrass 9.8, while phytotoxic effects on cotton were rated 3.5. An untreated plot was rated 3 for yellow nutsedge, 3.5 for barnyardgrass and 0 for cotton.

EXAMPLE 11

Several field plots of Drummer Silt loam containing about 5.5% organic matter and infested with yellow nutsedge were each prepared as for planting a crop. In each of two respective replicated plots, treatments were applied using a sufficiently concentrated emulsion of α-(2,2,2-trichloroethyl)-m-chlorostyrene to provide, respectively, 2 and 4 pounds per acre of active when applied at a spray volume of 25 gallons per acre using a bicycle sprayer. Each plot was 40 inches by 7 feet and replicated four times. Within one hour after each spray application, the styrene compound was incorporated into the soil to a depth of 3-4 inches by rototilling. Stand counts were taken after one month and also two months of the test plots and of several control plots. The average results show, after one month, 84 and 92% control of yellow nutsedge respectively for the application of 2 and 4 lbs/acre active, and, after two months, 79 and 93% control for the application of 2 and 4 lbs/acre active.

The compositions employed in each of Examples 3-11 were stable and conveniently employed in soil application. The other embodiments of the present composition described herein upon being substituted for the compositions described in the said examples provide for substantially the same uniformly excellent herbicidal results. The use of emulsifiable concentrates and water dispersions thereof is preferred.

What is claimed is:

1. A herbicidal composition which consists essentially of, by weight and in admixed form:

an effective amount, for the preemergent control of sedges and perennial grassy weeds by soil incorporation primarily above the underground stems and tubers of said sedges and grassy weeds, in the range of from about 0.005 to about 90 percent, of a meta-halostyrene selected from the group consisting of alpha-(2,2,2-trichloroethyl)-m-chlorostyrene, alpha-(2,2,2-trichloroethyl)-m-bromostyrene and a co-mixture thereof, and;

the balance a herbicide carrier selected from (a) a surface active dispersing means;

(b) a surface active dispersing means admixed with a liquid carrier selected from the group consisting of water, and a non-aqueous liquid, the non-aqueous liquid being selected from the group consisting of petroleum distillate, agricultural spray oil, kerosene, fuel oil, naphtha, xylene, chlorinated hydrocarbon, acetone, and ether of ethylene glycol;

(c) a surface active dispersing means admixed with a finely divided solid agricultural carrier;

(d) a finely divided solid agricultural carrier in the form of a dust; and (e) a finely divided solid agricultural carrier in granulated form, provided that the surface active dispersing means is provided in sufficient amount to emulsify or suspend the meta-halostyrene in any water present in the composition or a tank mix prepared therefrom.

and provided further that in an admixture containing finely divided solid agricultural carrier the proportion of meta-halostyrene does not exceed about 20 percent by weight.

2. The composition as in claim 1 wherein the meta-halostyrene is α-(2,2,2-trichloroethyl)meta-chlorostyrene.

3. The composition as in claim 1 wherein the meta-halostyrene is admixed substantially only with surface active dispersing means.

4. The composition as in claim 1 wherein the proportion of meta-halostyrene is in the range of about 0.005 to about 50 percent by weight.

5. The composition as in claim 4 wherein the meta-halostyrene is admixed with a surface active dispersing means admixed with a liquid carrier.

6. The composition as in claim 5 wherein the liquid carrier is water.

7. The composition as in claim 5 wherein the liquid carrier is non-aqueous.

8. The composition as in claim 7 wherein the non-aqueous liquid carrier is selected from the group consisting of, agricultural spray oil, petroleum distillate, chlorinated hydrocarbon and ether of ethylene glycol.

9. The composition as in claim 1 wherein the proportion of meta-halostyrene is in the range of about 0.018 to about 2.4 percent by weight.

10. The composition as in claim 9 in the form of a tank mix wherein the meta-halostyrene is admixed with surface active dispersing means and water, and any non-aqueous liquid contained in the concentrate from which the tank mix is prepared.

11. The composition as in claim 10 wherein the meta-halostyrene is α-(2,2,2-trichloroethyl)-meta-chlorostyrene.

12. The composition as in claim 1 wherein the surface active dispersing means is selected from the group consisting of (a) condensation product of alkylene oxide with a phenol and a carboxylic acid; (b) alkyl aryl sulfonate; (c) polyoxyalkylene derivative of sorbitan ester; (d) castor oil ethoxylate; (e) ether alcohol; (f) mahogany soap; (g) block copolymer of polyethylene oxide and polypropylene oxide; and (h) a combination of any two or more of items (a) through (g).

* * * * *